United States Patent

Bru-Magniez et al.

Patent Number: 5,418,242
Date of Patent: * May 23, 1995

[54] PIPERIDINYLTHIOINDOLE DERIVATIVES, THEIR METHODS OF PREPARATION AND PHARMACEUTICAL COMPOSITIONS IN WHICH THEY ARE PRESENT, USEFUL ESPECIALLY AS ANALGESICS

[75] Inventors: Nicole Bru-Magniez, Paris; Dominique Potin, Aubergenville; Jean-Marie Teulon, La Celle Saint Cloud, all of France

[73] Assignee: Laboratoires Upsa, Agen, France

[ * ] Notice: The portion of the term of this patent subsequent to May 31, 2011 has been disclaimed.

[21] Appl. No.: 228,289

[22] Filed: Apr. 15, 1994

Related U.S. Application Data

[63] Continuation-in-part of Ser. No. 81,704, Jun. 25, 1993, Pat. No. 5,317,025.

Foreign Application Priority Data

May 18, 1993 [FR] France ................. 93 05966

[51] Int. Cl.⁶ .................. A61K 31/445; C07D 401/12
[52] U.S. Cl. ..................... 514/323; 546/201
[58] Field of Search ......... 514/323; 546/201

[56] References Cited

U.S. PATENT DOCUMENTS 3,264,311 8/1966 Sjmusjkovicz .................. 546/201

OTHER PUBLICATIONS

Teikoku Horwone Mfg. Co. "3-Substituted-2-phenylindole derivatives" CA 104 50789a (1986).

*Primary Examiner*—Ceila Chang
*Attorney, Agent, or Firm*—Dennison, Meserole, Pollack & Scheiner

[57] ABSTRACT

The present invention relates to the derivatives of the formula

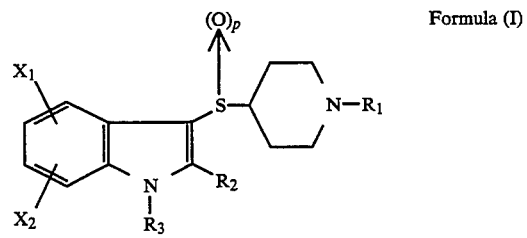

Formula (I)

and their addition salts, and to their use in therapeutics, especially as drugs with analgesic properties.

11 Claims, No Drawings

PIPERIDINYLTHIOINDOLE DERIVATIVES, THEIR METHODS OF PREPARATION AND PHARMACEUTICAL COMPOSITIONS IN WHICH THEY ARE PRESENT, USEFUL ESPECIALLY AS ANALGESICS

This application is a continuation-in-part of U.S. application Ser. No. 08/081,704, filed Jun. 25, 1993 now U.S. Pat. No. 5,317,025.

The present invention relates, by way of novel products, to the piperidinylthioindole derivatives of general formula (I) below and their addition salts, in particular the pharmaceutically acceptable addition salts.

The compounds in question have a very valuable pharmacological profile insofar as they possess analgesic properties. They will therefore be particularly indicated for the treatment of pain. There may be mentioned, for example, their use in the treatment of muscular, articular or neural algia, dental pain, herpes zoster and migraine, and in the treatment of rheumatic complaints and pain of cancerous origin, and also as complementary treatments in infectious and febrile states.

The present invention further relates to the method of preparing said products and to their applications in therapeutics.

These piperidinylthioindole derivatives have general formula (I):

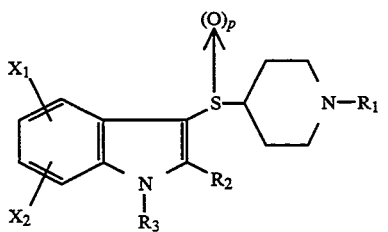

Formula (I)

in which:

$X_1$ and $X_2$ are independently:
- the hydrogen atom;
- a halogen atom;
- a lower alkyl radical having 1 to 6 carbon atoms;
- a trifluoromethyl group;
- a hydroxyl group;
- a lower O-alkyl radical having 1 to 6 carbon atoms;
- a nitrile group;
- an acid group;
- an amide group;
- a hydroxymethyl group;
- an aminomethyl group; or
- a sulfonamidomethyl group and can be located in the 4-, 5-, 6- or 7-position of the indole ring, $R_1$ is:
- the hydrogen atom;
- a lower alkyl radical having 1 to 6 carbon atoms;
- a methoxy group;
- a group —COR', in which R' is the hydrogen atom or a lower alkyl radical having 1 to 6 carbon atoms;
- a group —COOR'';
- a group —CSSR'',
  in which R'' is a lower alkyl radical having 1 to 6 carbon atoms, a vinyl radical or a phenyl;
- a group —CSSM, in which M is sodium or potassium;
- a radical —(CH$_2$)$_n$-phenyl; or
- a radical —(CH$_2$)$_n$-pyrrole,
  in which n is an integer from 0 to 4, $R_2$ is:
- the hydrogen atom;
- a lower alkyl radical having 1 to 6 carbon atoms; or
- a phenyl radical which is unsubstituted or substituted by a halogen atom, $R_3$ is:
- the hydrogen atom;
- a lower alkyl radical having 1 to 6 carbon atoms;
- a group COOR'', in which R'' is as defined above; or
- a radical —(CH$_2$)$_n$-phenyl, in which the phenyl is unsubstituted or substituted by a halogen atom, n being an integer from 0 to 4, and p is an integer from 0 to 2.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

Halogen is understood as meaning a chlorine, bromine, iodine or fluorine atom.

The following abbreviations have been used in the description:
Ph: phenyl
phenethyl: 2-phenylethyl
nBu: butyl
tBu: tert-butyl (1,1-dimethylethyl)
iPr: isopropyl (1-methylethyl)
Me: methyl
Et: ethyl
THF: tetrahydrofuran
Bn: benzyl
Ac: acetyl Advantageously, within the framework of the present invention, the compound of formula (I) used will be one in which at least one of the following conditions is satisfied:

$X_2$ is the hydrogen atom
$X_1$ is the chlorine atom in the 5-position of the indole ring
$X_1$ is the bromine atom in the 5-position of the indole ring
$X_1$ is the fluorine atom in the 5-position of the indole ring
$R_1$ is the hydrogen atom
$R_1$ is a methyl radical
$R_1$ is a benzyl group
$R_1$ is a carbonylvinyloxy group
$R_1$ is a methoxy group
$R_2$ is the hydrogen atom
$R_2$ is a methyl radical
$R_3$ is the hydrogen atom
$R_3$ is a methyl radical
p is equal to zero The particularly preferred compounds of the invention are selected from the products of the formulae

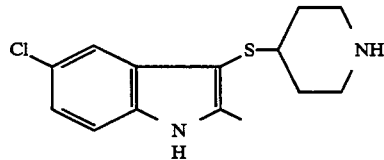

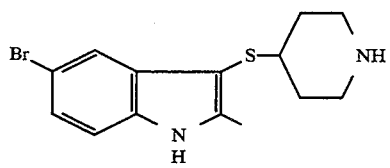

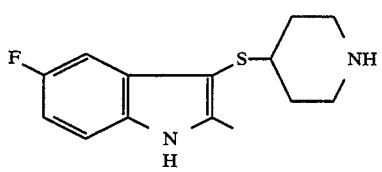

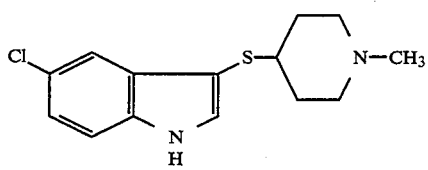

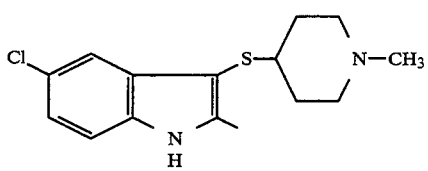

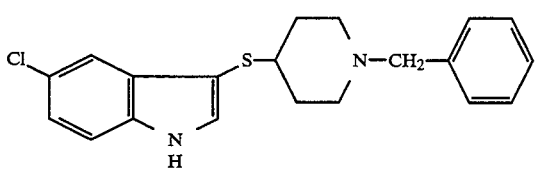

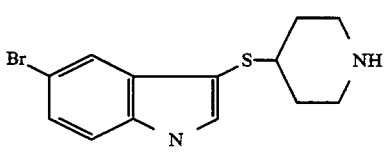

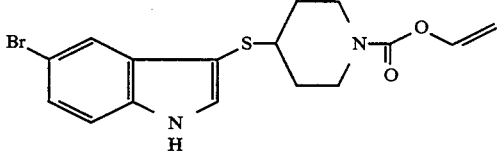

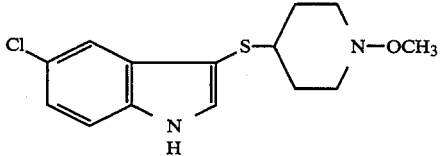

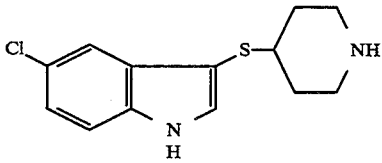

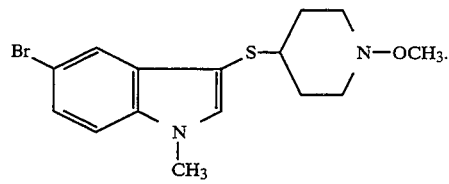

According to the invention, the compounds of formula (I) may be synthesized in the following manner:

Reaction of hydrogen sulfide in an alcohol such as, for example, isopropanol, at a temperature below 15° C., with the piperidin-4-ones of formula (II), followed by reduction with sodium or potassium borohydride in an alcohol such as, for example, isopropanol, will give the piperidine-4-thiols of formula (III) in accordance with the following scheme:

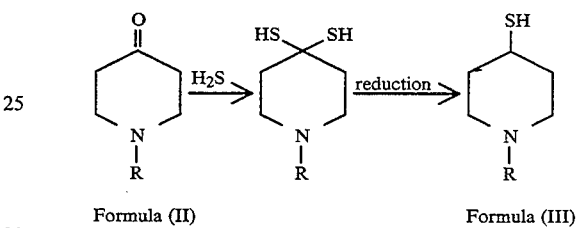

Formula (II)                Formula (III)

in which formulae (II) and (III), R is a lower alkyl radical having 1 to 6 carbon atoms, a benzyl radical, a phenethyl radical, a protecting group —COOtBu or a methoxy group.

The piperidinones of formula (II) are commercially available with the exception of the one in which R=—COOtBu, which is prepared by reacting ditert-butyl dicarbonate with piperidin-4-one or its commercially available monohydrate by the method described in the following literature reference: W. S. SAARI, W. HALCZENKO, J. R. HUFF, J. P. GUARE Jr, C. A. HUNT, W. C. RANDALL, V. J. LOTTI, G. G. YARBROUGH; J. Med. Chem. 1984, 27, 1182–5, and that in which R is a methoxy group, which was synthesized by the method described in the following reference: R. T. MAJOR, F. DÜRSCH; J. Org. Chem. 1961, 26, 1867–74.

The derivatives of formula (III) in which R is the hydrogen atom will be prepared from the derivatives of formula (III) in which R is a methyl radical by reaction with ethyl chloroformate in acetone, followed by a second treatment with ethyl chloroformate in toluene under reflux and then by a treatment with hydrochloric acid in acetic acid under reflux, in accordance with the following scheme:

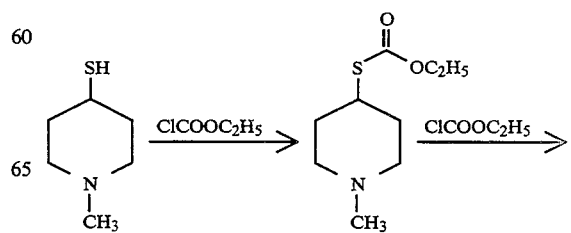

-continued

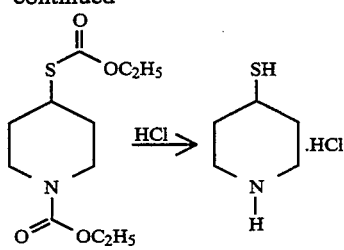

This preparative method is described in the following literature reference: J. ENGEL, A. BORK, I. NUBERT, H. SCHÖNENBERGER; Arch. Pharm. (Weinheim) 1988, 321, 821–2.

Reaction of the compounds of formula (III), in which R is a lower alkyl radical having 1 to 6 carbon atoms, a benzyl radical, a phenethyl radical, a protecting group —COOtBu or the hydrogen atom, with a halogenoketone of formula (IV):

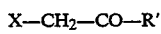      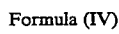

in which R' is a lower alkyl radical having 1 to 6 carbon atoms or a phenyl radical which is unsubstituted or substituted by a halogen atom and X is a halogen atom, optimally chlorine or bromine, will give the derivatives of formula (V):

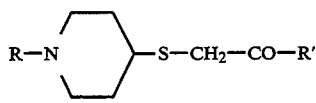     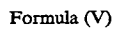

in which R and R' are as defined above.

This reaction is carried out in the presence of a sodium, potassium or lithium alcoholate in the corresponding alcohol or in tetrahydrofuran, or else by phase transfer in the presence of sodium or potassium carbonate and tetrabutylammonium iodide in toluene at temperatures between 20° and 130° C.

Reaction of the same compounds of formula (III) with a halogenoaldehyde whose aldehyde group is protected by ketalization, of formula (VI):

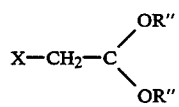     

in which R'' is a lower alkyl having 1 to 6 carbon atoms, optimally methyl or ethyl, or the two radicals R'' together form —CH$_2$—CH$_2$—, and X is a halogen atom, optimally chlorine or bromine, will give the derivatives of formula (VII):

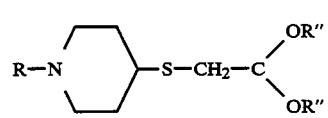     

in which R and R' are as defined above.

This reaction is carried out in the same way as for the halogenoketones, for example in the presence of sodium methylate in tetrahydrofuran.

The derivatives of formula (V) or formula (VII) will then be reacted with phenylhydrazines of formula (VIII):

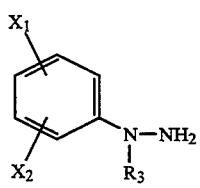

in which X$_1$, X$_2$ and R$_3$ are as defined above.

These phenylhydrazines are commercially available or can be prepared by the conventional methods known to those skilled in the art, for example by the diazotization of commercially available anilines of formula (IX):

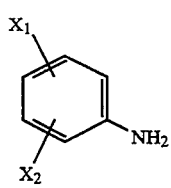

in which X$_1$ and X$_2$ are as defined above, with sodium nitrite in an acid medium, followed by treatment of the diazotized derivative with stannous chloride to give a phenylhydrazine of formula (X):

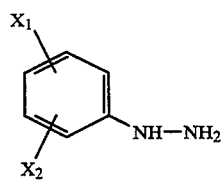

in which X$_1$ and X$_2$ are as defined above, after which this phenylhydrazine is optionally reacted with halogenated derivatives of formula (XI):

     Formula (XI)

in which R$_3$ is as defined above and X is a halogen atom, in liquid ammonia and/or tetrahydrofuran, in the presence of sodium amide, at a temperature of −40° C., the reaction mixture being left to return to room temperature.

The reaction of the derivatives of formula (V) or formula (VII) with the phenylhydrazines of formula (VIII) will be carried out under the conventional conditions of the Fischer synthesis for indole rings, optimally in the presence of gaseous hydrogen chloride in isopropanol at 0° C. in order to initiate the reaction, which will subsequently be performed at room temperature. This reaction gives the derivatives of formula (XII):

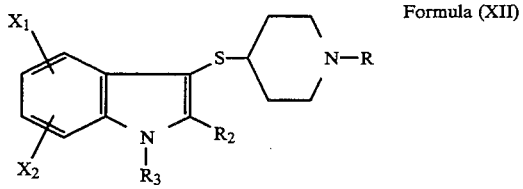

Formula (XII)

in which $X_1$, $X_2$, $R_2$ and $R_3$ are as defined in formula (I), R being a lower alkyl radical having 1 to 6 carbon atoms, a benzyl or phenethyl radical or the hydrogen atom.

When the indole formation reaction is performed with compounds in which R is the group —COOtBu, the compounds of formula (XII) in which R is the hydrogen atom will be obtained directly.

The compounds of formula (XII) in which R is the hydrogen atom may react with halides of formula (XIII):

$R_1X$  Formula (XIII)

in which $R_1$ is as defined above and X is a halogen atom, optimally chlorine, bromine or iodine, to give the compounds of formula (I) in which p is equal to zero, this reaction being carried out in the presence of a tertiary base such as triethylamine or pyridine, or sodium or potassium carbonate, in an inert solvent such as toluene or dichloromethane, at a temperature between room temperature and 130° C., with the exception of the cases where $R_1$ is the group CHO, for which the compounds of formula (XII) in which R is the hydrogen atom will be reacted with formic acid in dichloromethane in presence of dicyclohexylcarbodiimide, and where $R_1$ is the group CSSR'', for which the compounds of formula (XII) in which R is the hydrogen atom will be reacted with carbon disulfide in a basic medium, the resulting salt then reacting with an alkyl halide.

The compounds of formula (I) in which $X_1$ or $X_2$ is a nitrile group may be obtained from the compounds of formula (I) in which $X_1$ or $X_2$ is a halogen, preferably bromine or iodine, by refluxing with cuprous cyanide in N-methylpyrrolidone.

The compounds of formula (I) in which $X_1$ or $X_2$ is an acid group may be obtained from the compounds of formula (I) in which $X_1$ or $X_2$ is a halogen, preferably bromine or iodine, after metalation with nBuLi in tetrahydrofuran at −78° C., followed by carbonation with carbon dioxide, care being taken, if necessary, to protect the indole nitrogen with a protecting group such as a tosylate, COOtBu, COOBn or else t-butyldimethylsilane, and the piperidine nitrogen with COOtBu or COOBn, for example.

The compounds of formula (I) in which $X_1$ or $X_2$ is an amide group may be prepared under the same conditions as in the previous case, except that the compound metalated with nBuLi is reacted with trimethylsilyl isocyanate instead of being carbonated; they may also be obtained by conversion of the acid obtained above to the acid chloride, for example using thionyl chloride, followed by reaction of this acid chloride with an amine, for example ammonia.

The compounds of formula (I) in which $X_1$ or $X_2$ is an acid group may be reduced, for example with lithium aluminum hydride, to give the compounds in which $X_1$ or $X_2$ is a hydroxymethyl group.

The compounds of formula (I) in which $X_1$ or $X_2$ is a nitrile group may be reduced, for example with lithium aluminum hydride, to give the compounds in which $X_1$ or $X_2$ is an aminomethyl group, it being possible for these compounds to react with a sulfonyl chloride to give the compounds of formula (I) in which $X_1$ or $X_2$ is a sulfonamidomethyl group.

Another possible way of obtaining the latter compounds is to react the compounds of formula (I) in which $X_1$ or $X_2$ is a hydroxymethyl group with mesyl chloride or tosyl chloride, it being possible for the resulting mesylate or tosylate to react with a previously metalated sulfonamide to give these derivatives of formula (I) in which $X_1$ or $X_1$ is a sulfonamidomethyl group.

The compounds of formula (I) in which $X_1$ or $X_2$ is a hydroxyl group will be prepared from the derivatives in which $X_1$ or $X_2$ is a lower O-alkyl radical by reaction with boron tribromide in dichloromethane or chloroform.

The compounds of formula (I) in which $R_3$ is the hydrogen atom and p is equal to zero may be substituted in the 1-position of the indole with the derivatives of formula (XI) by the methods known to those skilled in the art, for example in the presence of a metalating agent such as sodium amide, sodium, potassium or lithium hydride or a sodium, potassium or lithium alcoholate, in a solvent such as liquid ammonia, tetrahydrofuran or dimethylformamide, at a temperature between −40° C. and 80° C., or in the presence of sodium hydroxide and a phase transfer agent in toluene.

The resulting compounds of formula (XIV):

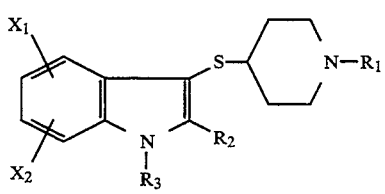

Formula (XIV)

in which $X_1$, $X_2$, $R_1$, $R_2$ and $R_3$ are as defined in formula (I), may be oxidized with an oxidizing agent such as metachloroperbenzoic acid in a solvent like chloroform or methylene chloride, or such as potassium peroxymonosulfate (KHSO$_5$) in an alcohol/water mixture, at a temperature between 0° and 30° C., to give the compounds of formula (I) in which p is equal to 1 or 2. The amount of oxidizing agent will be chosen so that p=1 or p=2.

The compounds of formula (I) as defined above, and their addition salts, in particular the pharmaceutically acceptable addition salts, possess a very good analgesic activity.

These properties justify their application in therapeutics and the invention further relates, by way of drugs, to the products as defined by formula (I) above, and their addition salts, in particular the pharmaceutically acceptable addition salts.

The addition salts of the compounds of formula (I) can be obtained by reacting these compounds with a mineral or organic acid by a method known per se. Among the acids which can be used for this purpose, there may be mentioned hydrochloric, hydrobromic, sulfuric, phosphoric, toluene-4-sulfonic, methanesulfonic, cyclohexylsulfamic, oxalic, succinic, formic, fumaric, maleic, citric, aspartic, cinnamic, lactic, glutamic, N-acetylaspartic, N-acetylglutamic, ascorbic, malic, benzoic, nicotinic and acetic acids.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal, ocular, nasal or auricular route.

These compositions can be solid or liquid and can be in the pharmaceutical forms commonly used in human medicine, such as, for example, simple or coated tablets, gelatin capsules, granules, suppositories, injectable preparations, transdermal systems, eye lotions, aerosols and sprays, and ear drops. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semi-synthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic activity affording especially a favorable treatment for pain, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with analgesic activity is prepared which affords especially a favorable treatment for pain.

In one variant, a pharmaceutical composition is formulated as gelatin capsules or tablets containing from 1 mg to 1000 mg of active ingredient, or as injectable preparations containing from 0.1 mg to 500 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels or aerosol preparations.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the afore-mentioned indications, orally in the form of tablets or gelatin capsules containing from 1 mg to 1000 mg of active ingredient, or parenterally in the form of injectable preparations containing from 0.1 mg to 500 mg of active ingredient, in one or more daily dosage units for an adult with an average weight of 60 to 70 kg.

In animal therapeutics, the daily dose which can be used is between 0.01 and 20 mg per kg.

Further characteristics and advantages of the invention will be understood more clearly from the following description of some Examples, which in no way imply a limitation but are given by way of illustration.

The method described in the literature (H. BARRERA, R. E. LYLE, J. Org. Chem. (1962) 27, 641-2) is used to prepare 1-methylpiperidine-4-thiol (formula III in which R=methyl) and the following thiols (Examples 1 to 5):

EXAMPLE 1

1-(Phenylmethyl)piperidine-4-thiol

R=CH$_2$PH                            Formula (III)

Oil.

$^1$H NMR (CDCl$_3$): 7.15–7.4 (m, 5H); 3.48 (s, CH$_2$ benz); 2.65–2.9 (m, 2CH+SCH); 1.9–2.15 (m, 4CH); 1.55–1.75 (m, 2CH); 1.5 (d, SH, J=7 Hz).

EXAMPLE 2

1-(2-Phenylethyl)piperidine-4-thiol

R=CH$_2$CH$_2$Ph                      Formula (III)

Oil.

$^1$H NMR (CDCl$_3$): 7.15–7.35 (m, 5H); 2.9–3.05 (m, 2CH); 2.65–2.9 (m, CH$_2$+SCH); 2.5–2.65 (m, CH$_2$); 1.95–2.25 (m, 4CH); 1.6–1.85 (m, 2CH); 1.54 (d, SH, J=7.1 Hz).

EXAMPLE 3

1,1-Dimethylethyl 4-mercaptopiperidine-1-carboxylate

R=CO$_2$tBu                           Formula (III)

Oil.

$^1$H NMR (CDCl$_3$): 155.0 (Cq); 79.7 (Cq); 43.6 (CHS); 36.5 (CH$_2$); 36.1 (CH$_2$); 28.5 (CH$_3$).

EXAMPLE 4

1-(1-Methylethyl)piperidine-4-thiol

R=iPr                                 Formula (III)

Oil.

$^1$H NMR (CDCl$_3$): 2.6–2.9 (m, 4H); 2.1–2.3 (m, 2CH); 1.95–2.1 (m, 2CH); 1.51 (d, SH, J=7.6 Hz); 1.5–1.75 (m, 2CH); 1.02 (d, 2CH$_3$, J=6.5 Hz).

EXAMPLE 5

1-Methoxypiperidine-4-thiol

R=OMe  Formula (III)

Synthesized from 1-methoxypiperidin-4-one prepared according to R. T. MAJOR, F. DÜRSCH; J. Org. Chem. (1961) 26, 1867–74.

Oil.

$^1$H NMR (CDCl$_3$): 3.55 (s, CH$_3$); 3.4–2.2 (m, 5H); 2.2–1.4 (m, 4H+5H).

EXAMPLE 6

1-Methyl-4-[(2-oxopropyl)thio]piperidine

R=Me, R'=Me  Formula (V)

Sodium methylate (5.9 g) is added in portions to a solution of 1-methylpiperidine-4-thiol (14 g) in anhydrous tetrahydrofuran (100 ml) at room temperature. After 2 hours at this temperature, chloroacetone (8.8 ml) is added dropwise. After 24 hours, the precipitate is filtered off and the filtrate is concentrated and chromatographed on silica gel (eluent: ethyl acetate, then ethanol) to give 1-methyl-4-[(2-oxopropyl)thio]piperidine (11.5 g) in the form of an oil.

$^1$H NMR (CDCl$_3$): 3.28 (s, CH$_2$S); 2.75–2.90 (m, 2H); 2.5–2.7 (m, CHS); 2.30 (s, CH$_3$N); 2.25 (s, CH$_3$); 1.85–2.15 (m, 4H); 1.5–1.75 (m, 2H).

The following compounds (Examples 7 and 8) were prepared by using the same method with the appropriate chloroketones and piperidine-4-thiols:

EXAMPLE 7

4-[(2-Oxopropyl)thio]piperidine

R=H, R'=Me  Formula (V)

Yellow solid: m.p.=136° C.
Hydrochloride: m.p.=118° C.

$^1$H NMR (CDCl$_3$): 3.2 (s, CH$_2$S); 2.95–3.1 (m, 2H); 2.45–2.75 (m, 3H+NH); 2.23 (s, CH$_3$); 1.7–1.95 (m, 2H); 1.25–1.5 (m, 2H).

EXAMPLE 8

4-[[2-(4-Chlorophenyl)-2-oxoethyl]thio]piperidine

R=H, R'=4-Cl-PH  Formula (V)

Orange solid: m.p.=202° C.

$^1$H NMR (CDCl$_3$): 7.9 (d, 2CH, J=8.5 Hz); 7.43 (d, 2CH, J=8.5 Hz); 3.75 (s, SCH$_2$); 2.95–3.25 (m, 2H+HN); 2.7–2.9 (m, SCH); 2.5–2.7 (m, 2CH); 1.85–2.05 (m, 2CH); 1.35–1.6 (m, 2CH).

EXAMPLE 9

4-[(2-Oxopropyl)thio]-1-(phenylmethyl)piperidine

R=CH$_2$Ph, R'=Me  Formula (V)

A suspension of 1-(phenylmethyl)piperidine-4-thiol (70 g, prepared in Example 1), chloroacetone (26.9 ml), sodium carbonate (71.6 g) and tetrabutylammonium iodide (31.2 g) in toluene (350 ml) is stirred at room temperature for 4 hours. The insoluble material is filtered off and washed with toluene. After concentration, the filtrate is taken up in dichloromethane and washed with dilute sodium hydroxide and then with a saturated aqueous solution of sodium chloride. After drying over sodium sulfate, the solution is concentrated to give 4-[(2-oxopropyl)thio]-1-(phenylmethyl)piperidine (82.2 g) in the form of an oil, which is sufficiently pure to be used in the next step.

$^1$H NMR (CDCl$_3$): 7.15–7.35 (m, 5H); 3.5 (s, CH$_2$ benz); 3.2 (s, SCH$_2$); 2.75–2.95 (m, 2H); 2.55–2.75 (m, SCH); 2.28 (s, CH$_3$); 1.85–2.15 (m, 4H); 1.5–1.75 (m, 2CH).

The following compounds (Examples 10 and 11) were prepared by using the same method of synthesis with the appropriate piperidine-4-thiols:

EXAMPLE 10

4-[(2-Oxopropyl)thio]-1-(2-phenylethyl)piperidine

R=CH$_2$CH$_2$Ph, R'=Me  Formula (V)

Oil.

$^1$H NMR (CDCl$_3$): 7.1–7.35 (m, 5H); 3.27 (s, SCH$_2$); 2.85–3.05 (m, 2H); 2.75–2.85 (m, 2H); 2.5–2.75 (m, 3H); 2.29 (s, CH$_3$); 1.9–2.2 (m, 4H); 1.5–1.8 (m, 2H).

EXAMPLE 11

1,1-Dimethylethyl 4-[(2-oxopropyl)thio]piperidine-1-carboxylate

R=CO$_2$tBu, R'=Me  Formula (V)

Oil.

$^1$H NMR (CDCl$_3$): 3.9–4.05 (m, 2CH); 3.26 (s, SCH$_2$); 2.7–3 (m, 2CH+SCH); 2.32 (s, CH$_3$); 1.85–2 (m, 2CH); 1.35–1.6 (m, 2CH); 1.45 (s, 3CH$_3$).

EXAMPLE 12

4-[(2,2-Diethoxyethyl)thio]-1-methylpiperidine

R=Me, R''=Et  Formula (VII)

Sodium methylate (18.1 g) is added in portions to a solution of 1-methylpiperidine-4-thiol (22 g) in anhydrous tetrahydrofuran (200 ml). After one hour, the diethyl acetal of bromoacetaldehyde (30.3 ml) is added. After 4 hours at room temperature, the solution is heated for 2 hours at 40° C. The insoluble material is filtered off and rinsed with THF. The filtrate is concentrated and then distilled under reduced pressure to give 4-[(2,2-diethoxyethyl)thio]-1-methylpiperidine (36 g; b.p.=104°–108° C. under 0.05 atm) in the form of an oil.

$^1$H NMR (CDCl$_3$): 4.6 (t, 1H, J=5.6 Hz); 3.45–3.8 (m, 2CH$_2$O); 2.65–2.9 (m, 3CH); 2.72 (d, SCH$_2$, J=5.6 Hz); 2.26 (s, NCH$_3$); 1.9–2.1 (m, 4CH); 1.5–1.75 (m, 2CH); 1.22 (t, 2CH$_3$, J=7 Hz).

Compounds 13 to 16 are also prepared by using the same method:

EXAMPLE 13

4-[(2,2-Diethoxyethyl)thio]-1-(phenylmethyl)piperidine

R=CH$_2$Ph, R''=Et  Formula (VII)

Oil.

$^1$H NMR (CDCl$_3$): 7.2–7.4 (m, 5H); 4.6 (t, 1H, J=5.6 Hz); 3.46 (s, CH$_2$ benz); 3.5–3.8 (m, 2CH$_2$O); 2.65–2.95 (m, 4H); 2.75 (d, SCH$_2$, J=5.6 Hz); 1.85–2.15 (m, 4H); 1.5–1.8 (m, 2H); 1.22 (t, 2CH$_3$, J=7 Hz).

EXAMPLE 14

4-[(2,2-Diethoxyethyl)thio]-1-(1-methylethyl)piperidine

R=iPr, R''=Et  Formula (VII)

Oil.

$^1$H NMR (CDCl$_3$): 4.60 (t, 1H, J=5.6 Hz); 3.45–3.75 (m, 2CH$_2$O); 2.6–2.9 (m, 4H); 2.73 (d, CH$_2$S, J=5.6 Hz); 2.1–2.25 (m, 2CH); 1.9–2.05 (m, 2CH); 1.5–1.7 (m, 2CH); 1.22 (t, 2CH$_3$, J=7 Hz); 1.02 (d, 2CH$_3$, J=6.6 Hz).

EXAMPLE 15

4-[(2,2-Diethoxyethyl)thio]-1-methoxypiperidine

R=OMe, R″=Et                Formula (VII)

Oil.

$^1$H NMR (CDCl$_3$): 4.55 (t, 1H, J=5.6 Hz); 3.8–3.4 (m, 4H, 2CH$_2$O); 3.46 (s, 3H, OCH$_3$); 3.4–2.9 (m, 3H); 2.8–2.6 (m, 3H); 2.5–1.4 (m, 5H); 1.2 (t, 2CH$_3$, J=7 Hz).

EXAMPLE 16

4-[(2,2-Diethoxyethyl)thio]piperidine

R=H, R″=Et                Formula (VII)

Oil.

$^1$H NMR (CDCl$_3$): 4.6 (t, 1H, J=5.5 Hz); 3.8–3.45 (m, 4H, 2CH$_2$O); 3.2–3.05 (m, 2CHN); 2.95–2.8 (m, CHS); 2.75 (d, CH$_2$S, J=5.5 Hz); 2.7–2.55 (m, 2CHN); 2.05–1.9 (m, 2CH); 1.6–1.35 (m, 2CH); 1.22 (t, 2CH$_3$, J=6.5 Hz).

EXAMPLE 17

2,5-Dimethyl-3-[[1-(phenylmethyl)piperidin-4-yl]thio]-1H-indole hydrochloride

R$_1$=Bn, R$_2$=Me, R$_3$=H, X$_1$=5-Me, X$_2$=H, p=0 Formula (I)

Paratolylhydrazine hydrochloride (20 g) is added to a solution of 4-[(2-oxopropyl)thio]-1-(phenylmethyl)-piperidine (33.2 g, prepared in Example 9) in isopropanol (150 ml) under nitrogen. After 30 minutes, the solution is cooled to 0° C. and saturated with gaseous hydrogen chloride. After 4 hours at room temperature, the precipitate formed is filtered off, washed with water and then taken up in hot ethanol. After cooling, the white crystals of 2,5-dimethyl-3-[[1-(phenylmethyl)-piperidin-4-yl]thio]-1H-indole hydrochloride (28.3 g) are filtered off.

C$_{22}$H$_{26}$N$_2$S.HCl.
M.p.=258° C.

The following compounds (Examples 18 to 35) were prepared by using the same method of synthesis with the appropriate hydrazines and ketones:

EXAMPLE 18

5-Chloro-2-methyl-3-(piperidin-4-ylthio)-1H-indole

R$_1$=H, R$_2$=Me, R$_3$=H, X$_1$=5-Cl, X$_2$=H, p=0   Formula (I)

Off-white solid.
C$_{14}$H$_{17}$ClN$_2$S.
M.p.=198°–199° C.

EXAMPLE 19

5-Fluoro-2-methyl-3-(piperidin-4-ylthio)-1H-indole

R$_1$=H, R$_2$=Me, R$_3$=H, X$_1$=5-F, X$_2$=H, p=0   Formula (I)

White solid.
C$_{14}$H$_{17}$FN$_2$S.
M.p.=201° C. (purified by chromatography on silica gel with the following eluent: CHCl$_3$/MeOH/NH$_4$OH:80/20/1).

EXAMPLE 20

5-Methoxy-2-methyl-3-(piperidin-4-ylthio)-1H-indole

R$_1$=H, R$_2$=Me, R$_3$=H, X$_1$=5-OMe, X$_2$=H, p=0 Formula (I)

Pale yellow solid.
C$_{15}$H$_{20}$N$_2$OS.
M.p.=217°–218° C. (recrystallized from xylene).

EXAMPLE 21

2-Methyl-3-(piperidin-4-ylthio)-5-(trifluoromethyl)-1H-indole hydrochloride

R$_1$=H, R$_2$=Me, R$_3$=H, X$_1$=5-CF$_3$, X$_2$=H, p=0 Formula (I)

White solid.
C$_{15}$H$_{17}$F$_3$N$_2$S.HCl.
M.p.=298°–301° C. (recrystallized from water).

EXAMPLE 22

5,7-Dichloro-2-methyl-3-(piperidin-4-yl-thio)-1H-indole hydrochloride

R$_1$=H, R$_2$=Me, R$_3$=H, X$_1$=5-Cl, X$_2$=7-Cl, p=0 Formula (I)

Beige solid.
C$_{14}$H$_{16}$Cl$_2$N$_2$S.HCl.
M.p.>275° C.

EXAMPLE 23

4,6-Dichloro-2-methyl-3-(piperidin-4-yl-thio)-1H-indole hydrochloride

R$_1$=H, R$_2$=Me, R$_3$=H, X$_1$=4-Cl, X$_2$=6-Cl, p=0 Formula (I)

Beige solid.
C$_{14}$H$_{16}$Cl$_2$N$_2$S.HCl.
M.p.>275° C.

EXAMPLE 24

5-Chloro-2-(4-chlorophenyl)-3-(piperidin-4-ylthio)-1H-indole

R$_1$=H, R$_2$=4-Cl-Ph, R$_3$=H, X$_1$=5-Cl, X$_2$=H,
p=0                Formula (I)

Pale yellow solid.
C$_{19}$H$_{18}$Cl$_2$N$_2$S.
M.p.=230°–231° C. (recrystallized from xylene).

EXAMPLE 25

5-Chloro-1-[(4-chlorophenyl)methyl]-2-methyl-3-(piperidin-4-ylthio)-1H-indole

R$_1$=H, R$_2$=Me, R$_3$=4-Cl-Bn, X$_1$=5-Cl, X$_2$=H,
p=0                Formula (I)

White solid.
C$_{21}$H$_{22}$Cl$_2$N$_2$S.
M.p.=122° C.

EXAMPLE 26

5-Chloro-2-methyl-3-[(1-methylpiperidin-4-yl)thio]-1H-indole

R$_1$=Me, R$_2$=Me, R$_3$=H, X$_1$=5-Cl, X$_2$=H, p=0 Formula (I)

Beige solid.
C$_{15}$H$_{19}$ClN$_2$S.
M.p.=154°–157° C. (recrystallized from cyclohexane).

EXAMPLE 27

5-Fluoro-2-methyl-3-[(1-methylpiperidin-4-yl)thio]-1H-indole $R_1$=Me, $R_2$=Me, $R_3$=H, $X_1$=5-F, $X_2$=H, p=0   Formula (I)

Pale yellow solid.
$C_{15}H_{19}FN_2S$.
M.p.=158°–159° C. (recrystallized from cyclohexane).

EXAMPLE 28

5-Bromo-2-methyl-3-[[1-(phenylmethyl)piperidin-4-yl]thio]-1H-indole hydrochloride $R_1$=Bn, $R_2$=Me, $R_3$=H, $X_1$=5-Br, $X_2$=H, p=0   Formula (I)

White solid.
$C_{21}H_{23}BrN_2S \cdot HCl$.
M.p.=266°–267° C.

EXAMPLE 29

5-Chloro-2,7-dimethyl-3-[[1-(phenylmethyl)piperidin-4-yl]thio]-1H-indole hydrochloride $R_1$=Bn, $R_2$=Me, $R_3$=H, $X_1$=5-Cl, $X_2$=7-Me, p=0   Formula (I)

White solid.
$C_{22}H_{25}ClN_2S \cdot HCl$.
M.p.=245°–246° C. (recrystallized from acetonitrile).

EXAMPLE 30

7-Chloro-2-methyl-3-[[1-(phenylmethyl)piperidin-4-yl]thio]-1H-indole $R_1$=Bn, $R_2$=Me, $R_3$=H, $X_1$=7-Cl, $X_2$=H, p=0   Formula (I)

White solid.
$C_{21}H_{23}ClN_2S$.
M.p.=133°–134° C. (recrystallized from ethanol).

EXAMPLE 31

4,7-Dichloro-2-methyl-3-[[1-(phenylmethyl)piperidin-4-yl]thio]-1H-indole hydrochloride $R_1$=Bn, $R_2$=Me, $R_3$=H, $X_1$=4-Cl, $X_2$=7-Cl, p=0   Formula (I)

Beige solid.
$C_{21}H_{22}Cl_2N_2S \cdot HCl$.
M.p.=143°–144° C.

EXAMPLE 32

5-Chloro-1,2-dimethyl-3-[[1-(phenylmethyl)piperidin-4-yl]thio]-1H-indole hydrochloride $R_1$=Bn, $R_2$=Me, $R_3$=Me, $X_1$=5-Cl, $X_2$=H, p=0   Formula (I)

White solid.
$C_{22}H_{25}ClN_2S \cdot HCl$.
M.p.=231°–233° C.

EXAMPLE 33

5-Chloro-2-methyl-3-[[1-(2-phenylethyl)piperidin-4-yl]thio]-1H-indole $R_1$=$CH_2CH_2Ph$, $R_2$=Me, $R_3$=H, $X_1$=5-Cl, $X_2$=H, p=0   Formula (I)

Pale yellow solid.
$C_{22}H_{25}ClN_2S$.
M.p.=190°–192° C.

EXAMPLE 34

5-Bromo-2-methyl-3-[[1-(2-phenylethyl)piperidin-4-yl]thio]-1H-indole $R_1$=$CH_2CH_2Ph$, $R_2$=Me, $R_3$=H, $X_1$=5-Br, $X_2$=H, p=0   Formula (I)

White solid.
$C_{22}H_{25}BrN_2S$.
M.p.=188°–189° C. (recrystallized from acetonitrile).

EXAMPLE 35

5-Chloro-1,2-dimethyl-3-[[1-(2-phenylethyl)piperidin-4-yl]thio]-1H-indole $R_1$=$CH_2CH_2Ph$, $R_2$=Me, $R_3$=Me, $X_1$=5-Cl, $X_2$=H, p=0   Formula (I)

White solid.
$C_{23}H_{27}ClN_2S$.
M.p.=136°–137° C. (recrystallized from acetonitrile).

EXAMPLE 36

5-Chloro-3-[[1-(phenylmethyl)piperidin-4-yl]thio]-1H-indole hydrochloride $R_1$=Bn, $R_2$=H, $R_3$=H, $X_1$=5-Cl, $X_2$=H, p=0   Formula (I)

4-Chlorophenylhydrazine hydrochloride (1 g) and 4-[(2,2-diethoxyethyl)thio]-1-(phenylmethyl)piperidine (1.8 g, prepared in Example 13) in isopropanol (20 ml) are stirred at room temperature under nitrogen until a solution is formed. After cooling to 0° C., the solution is saturated with gaseous hydrogen chloride. After 4 hours, the precipitate is filtered off, taken up in sodium hydroxide and extracted with ether and then with ethyl acetate. The combined organic phases are dried over sodium sulfate and concentrated. The residual oil is taken up in a solution of hydrogen chloride in ether to give 5-chloro-3-[[1-(phenylmethyl)piperidin-4-yl]thio]-1H-indole hydrochloride (1.4 g).

White solid.
$C_{20}H_{21}ClN_2S \cdot HCl \cdot 0.5H_2O$.
M.p.=158°–160° C.

The following compounds (Examples 37 to 52) were prepared by using the same method of synthesis with the appropriate hydrazines and acetals:

EXAMPLE 37

5-Bromo-3-[[1-(phenylmethyl)piperidin-4-yl]thio]-1H-indole $R_1$=Bn, $R_2$=H, $R_3$=H, $X_1$=5-Br, $X_2$=H, p=0   Formula (I)

White solid.
$C_{20}H_{21}BrN_2S$.
M.p.=134°–135° C. (recrystallized from cyclohexane).

EXAMPLE 38

3-[[1-(Phenylmethyl)piperidin-4-yl]thio]-5-(trifluoromethyl)-1H-indole $R_1$=Bn, $R_2$=H, $R_3$=H, $X_1$=5-$CF_3$, $X_2$=H, p=0   Formula (I)

White solid.
$C_{21}H_{21}F_3N_2S$.
M.p.=154°–155° C. (recrystallized from cyclohexane).

EXAMPLE 39

1-Phenyl-3-[[1-(phenylmethyl)piperidin-4-yl]thio]-1H-indole oxalate $R_1$=Bn, $R_2$=H, $R_3$=Ph, $X_1$=H, $X_2$=H, p=0  Formula (I)

Beige solid.
$C_{26}H_{26}N_2S \cdot C_2H_2O_4$.
M.p.=193°–194° C. (recrystallized from ether).

EXAMPLE 40

5-Chloro-3-[(1-methylpiperidin-4-yl)thio]-1H-indole $R_1$=Me, $R_2$=H, $R_3$=H, $X_1$=5-Cl, $X_2$=H, p=0  Formula (I)

Off-white solid.
$C_{14}H_{17}ClN_2S$.
M.p.=136°–137° C. (recrystallized from cyclohexane).

EXAMPLE 41

5-Methoxy-3-[(1-methylpiperidin-4-yl)thio]-1H-indole $R_1$=Me, $R_2$=H, $R_3$=H, $X_1$=5-OMe, $X_2$=H, p=0 Formula (I)

Beige solid.
$C_{15}H_{20}N_2OS$.
M.p.=153° C. (recrystallized from isopropanol).

EXAMPLE 42

3-[(1-Methylpiperidin-4-yl)thio]-1H-indole $R_1$=Me, $R_2$=H, $R_3$=H, $X_1$=H, $X_2$=H, p=0  Formula (I)

Pale yellow solid.
M.p.=143°–144° C. (recrystallized from cyclohexane).

EXAMPLE 43

5-(1-Methylethyl)-3-[(1-methylpiperidin-4-yl)thio]-1H-indole $R_1$=Me, $R_2$=H, $R_3$=H, $X_1$=5-iPr, $X_2$=H, p=0  Formula (I)

Off-white solid.
M.p.=110° C.

EXAMPLE 44

5-Bromo-3-[(1-methylpiperidin-4-yl)thio]-1H-indole $R_1$=Me, $R_2$=H, $R_3$=H, $X_1$=5-Br, $X_2$=H, p=0  Formula (I)

Light beige solid.
M.p.=135°–136° C. (recrystallized from cyclohexane).

EXAMPLE 45

5-Methyl-3-[(1-methylpiperidin-4-yl)thio]-1H-indole $R_1$=Me, $R_2$=H, $R_3$=H, $X_1$=5-Me, $X_2$=H, p=0  Formula (I)

White solid.
$C_{15}H_{20}N_2S$.
M.p.=134° C. (recrystallized from toluene).

EXAMPLE 46

5-Iodo-3-[(1-methylpiperidin-4-yl)thio]-1H-indole $R_1$=Me, $R_2$=H, $R_3$=H, $X_1$=5-I, $X_2$=H, p=0  Formula (I)

White solid.
$C_{14}H_{17}IN_2S$.
M.p.=136°–137° C.

EXAMPLE 47

5-Bromo-3-[[1-(1-methylethyl)piperidin-4-yl]thio]-1H-indole $R_1$=iPr, $R_2$=H, $R_3$=H, $X_1$=5-Br, $X_2$=H, p=0  Formula (I)

Beige solid.
$C_{16}H_{21}BrN_2S$.
M.p.=116°–118° C. (recrystallized from acetonitrile).

EXAMPLE 48

5-Chloro-3-[[1-(1-methylethyl)piperidin-4-yl]thio]-1H-indole $R_1$=iPR, $R_2$=H, $R_3$=H, $X_1$=5-Cl, $X_2$=H, p=0  Formula (I)

Light beige solid.
$C_{16}H_{21}ClN_2S$.
M.p.=123° C. (recrystallized from cyclohexane).

EXAMPLE 49

5-Bromo-3-(piperidin-4-ylthio)-1H-indole $R_1$=H, $R_2$=H, $R_3$=H, $X_1$=5-Br, $X_2$=H, p=0  Formula (I)

White solid.
$C_{13}H_{15}BrN_2S$.
M.p.=180°–181° C. (recrystallized from toluene).

EXAMPLE 50

5-Chloro-3-(piperidin-4-ylthio)-1H-indole hydrochloride $R_1$=H, $R_2$=H, $R_3$=H, $X_1$=5-Cl, $X_2$=H, p=0  Formula (I)

White solid.
$C_{13}H_{15}ClN_2S \cdot HCl$.
M.p.=251°–252° C. (recrystallized from ethanol).

EXAMPLE 51

5-Bromo-3-[(1-methoxypiperidin-4-yl)thio]-1H-indole $R_1$=OMe, $R_2$=H, $R_3$=H, $X_1$=5-Br, $X_2$=H, p=0 Formula (I)

Beige solid.
$C_{14}H_{17}BrN_2OS$.
M.p.=134°–135° C. (recrystallized from cyclohexane).

EXAMPLE 52

5-Chloro-3-[(1-methoxypiperidin-4-yl)thio]-1H-indole $R_1$=OMe, $R_2$=H, $R_3$=H, $X_1$=5-Cl, $X_2$=H, p=0 Formula (I)

Beige solid.
$C_{14}H_{17}ClN_2OS$.
M.p.=132° C.

EXAMPLE 53

5-Bromo-2-methyl-3-(piperidin-4-ylthio)-1H-indole $R_1$=H, $R_2$=Me, $R_3$=H, $X_1$=5-Br, $X_2$=H, p=0  Formula (I)

4-Bromophenylhydrazine hydrochloride (11.5 g) is solubilized in a solution of 1,1-dimethylethyl 4-[(2-oxopropyl)thio]piperidine-1-carboxylate (14 g, prepared in Example 11) in isopropanol (100 ml) under nitrogen. The solution is cooled to 0° C. and saturated with gaseous hydrogen chloride. After 4 hours at room temperature, the precipitate is filtered off, taken up in sodium hydroxide and extracted with ether and then with methylene chloride. The organic phases are combined, dried over sodium sulfate and concentrated. The solid obtained is taken up in the minimum amount of ether and recrystallized from xylene to give 5-bromo-2-methyl-3-(piperidin-4-ylthio)-1H-indole (9.5 g).

Pale yellow solid.
$C_{14}H_{17}BrN_2S$.
M.p.=207°-208° C.

EXAMPLE 54

5-Chloro-2-methyl-3-[[1-[2-(1H-pyrrol-1-yl)ethyl]-piperidin-4-yl]thio]-1H-indole

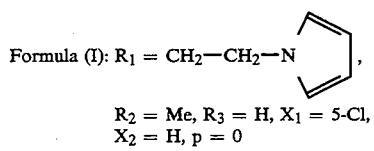

Formula (I): $R_1 = CH_2-CH_2-N$ ⟨pyrrole⟩, $R_2$ = Me, $R_3$ = H, $X_1$ = 5-Cl, $X_2$ = H, p = 0

A toluene solution (100 ml) of 5-chloro-2-methyl-3-(piperidin-4-ylthio)-1H-indole (1.09 g, prepared in Example 18), sodium carbonate (0.78 g) and 1-(2-iodoethyl)-1H-pyrrole (0.92 g, prepared according to GALEAZZI, E.; GUZMAN, A.; PINEDO, A.; SALDANA, A.; TORRE, D.; MUCHOWSKI, J. M., Can. J. Chem. (1983) 61, 454–60) is refluxed for 15 hours. The reaction mixture is taken up in a water/dichloromethane mixture. The organic phase is dried over magnesium sulfate and concentrated. The residue is chromatographed on silica gel (eluent: $CH_2Cl_2/MeOH$:90/10) to give 5-chloro-2-methyl-3-[[1-[2-(1H-pyrrol-1-yl)ethyl]-piperidin-4-yl]thio]-1H-indole (0.9 g).

Off-white solid.
$C_{20}H_{24}ClN_3S$.
M.p.=169°-171° C.

Using an analogous method, the product of Example 55 is obtained by reacting iodoethane with 5-chloro-3-(piperidin-4-ylthio)-1H-indole (prepared in Example 50):

Example 55

5-Chloro-3-[(1-ethylpiperidin-4-yl)thio]-1H-indole hydrochloride $R_1$=Et, $R_2$=H, $R_3$=H, $X_1$=5-Cl, $X_2$=H, p=0   Formula (I)

White solid.
$C_{15}H_{19}ClN_2S.HCl.\frac{1}{2}H_2O$.
M.p.=75°-77° C.

EXAMPLE 56

3-[[1-(Phenylmethyl)piperidin-4-yl]thio]-1,2,5-trimethyl-1H-indole $R_1$=Bn, $R_2$=Me, $R_3$=Me, $X_1$=5-Me, $X_2$=H, p=0 Formula (I)

An aqueous solution (200 ml) of 2,5-dimethyl-3-[[1-(phenylmethyl)piperidin-4-yl]thio]-1H-indole hydrochloride (prepared in Example 17) is rendered basic to pH 9 with sodium hydroxide. After extraction with ether, the organic phase is dried over sodium sulfate and concentrated. The indole crystallizes (10.4 g) after the addition of heptane.

A solution of this indole (10 g) in anhydrous tetrahydrofuran (50 ml) is added dropwise to a solution of sodium amide (1.3 g) in liquid ammonia (20 ml) at −40° C. After 10 minutes, methyl iodide (2 ml) in tetrahydrofuran (50 ml) is added.

After 2 hours at room temperature, 10 ml of water are added. After concentration, the mixture is taken up in water and extracted with ethyl acetate. The organic phase is dried over sodium sulfate and concentrated. 3-[[1-(Phenylmethyl)piperidin-4-yl]thio]-1,2,5-trimethyl-1H-indole (8.3 g) is obtained after recrystallization from ethanol.

White solid.
$C_{23}H_{28}N_2S$.
M.p.=134°-135° C.

Using a similar method, compounds 57 to 59 are prepared from the compounds of Examples 40, 44 and 51:

EXAMPLE 57

5-Chloro-1-methyl-3-[(1-methylpiperidin-4-yl)thio]-1H-indole $R_1$=Me, $R_2$=H, $R_3$=Me, $X_1$=5-Cl, $X_2$=H, p=0 Formula (I)

White solid.
$C_{15}H_{19}ClN_2S$.
M.p.=78°-79° C. (recrystallized from heptane).

EXAMPLE 58

5-Bromo-1-methyl-3-[(1-methylpiperidin-4-yl)thio]-1H-indole $R_1$=Me, $R_2$=H, $R_3$=Me, $X_1$=5-Br, $X_2$=H, p=0 Formula (I)

White solid.
$C_{15}H_{19}BrN_2S$.
M.p.=83°-84° C. (recrystallized from heptane).

EXAMPLE 59

5-Bromo-3-[(1-methoxypiperidin-4-yl)thio]-1-methyl-1H-indole $R_1$=OMe, $R_2$=H, $R_3$=Me, $X_1$=5-Br, $X_2$=H, p=0 Formula (I)

Beige solid.
$C_{15}H_{19}BrN_2OS$.
M.p.=84° C.

EXAMPLE 60

5-Chloro-2-methyl-3-(piperidin-4-ylsulfinyl)-1H-indole $R_1$=H, $R_2$=Me, $R_3$=H, $X_1$=5-Cl, $X_2$=H, p=1  Formula (I)

Metachloroperbenzoic acid (2.79 g) is added in portions to a solution of 5-chloro-2-methyl-3-(piperidin-4-ylthio)-1H-indole (3 g, prepared in Example 18) in dichloromethane (25 ml) at −40° C. After 4 hours at room temperature, the insoluble material is filtered off. The filtrate is washed with sodium hydroxide and then with water. The aqueous phases are extracted with ether and then with ethyl acetate. The organic phases are combined, dried over magnesium sulfate and concentrated. The oily residue obtained is chromatographed on silica gel (eluent: $CH_2Cl_2/MeOH/NH_4OH$:90/10/1) to give 5-chloro-2-methyl-3-(piperidin-4-yl-sulfinyl)-1H-indole in the form of an oil, which crystallizes on the addition of ether (0.4 g).

Beige solid.
$C_{14}H_{17}ClN_2OS.H_2O$.
M.p.=140°-145° C.

Using a similar method, the compound of Example 61 is prepared from the product of Example 49:

EXAMPLE 61

5-Bromo-3-[(1-methylpiperidin-4-yl)sulfinyl]-1H-indole $R_1$=Me, $R_2$=H, $R_3$=H, $X_1$=5-Br, $X_2$=H, p=1   Formula (I)

White solid.
$C_{14}H_{17}BrN_2OS$.
M.p.=215°–216° C.

EXAMPLE 62

5-(1-Methylethyl)-3-[(1-methylpiperidin-4-yl)sulfonyl]-1H-indole $R_1$=Me, $R_2$=H, $R_3$=H, $X_1$=5-iPr, $X_2$=H, p=2   Formula (I)

A solution of potassium peroxymonosulfate (49.5% KHSO$_5$, 21.2 g) in water (95 ml) is added drop-wise at 0° C. to a methanolic solution (95 ml) of 5-(1-methylethyl)-3-[(1-methylpiperidin-4-yl)thio]-1H-indole (7.5 g, prepared in Example 43). After 4 hours at room temperature, the white precipitate is filtered off and the filtrate is concentrated, rendered basic with sodium carbonate and extracted with ethyl acetate. The organic phase is dried over sodium sulfate and concentrated. 5-(1-Methylethyl)-3-[(1-methylpiperidin-4-yl)sulfonyl]-1H-indole (2.4 g) is obtained after purification on silica gel (eluent: CH$_2$Cl$_2$/iPrNH$_2$ 95/5).

Beige solid.
$C_{17}H_{24}N_2O_2S$.
M.p.=127°–129° C.

EXAMPLE 63

3-[(1-Methylpiperidin-4-yl)thio]-1H-indole-5-carbonitrile oxalate $R_1$=Me, $R_2$=H, $R_3$=H, $X_1$=5-CN, $X_2$=H, p=0 Formula (I)

A suspension of copper cyanide (17.7 g) and 5-bromo-3-[(1-methylpiperidin-4-yl)thio]-1H-indole (35.5 g, prepared in Example 44) in 1-methylpyrrolidin-2-one (45 ml) is refluxed for 24 hours. After dilution with water, the brown precipitate is separated off and then taken up with a mixture of water (110 ml) and ethylenediamine (170 ml). The blue solution is extracted with ethyl acetate. The organic phase is dried over sodium sulfate and concentrated. The residual oil is chromatographed on silica gel (eluent: AcOEt/iPrNH$_2$ 95/5) to give 3-[(1-methylpiperidin-4-yl)thio]-1H-indole-5-carbonitrile (1.5 g), which is converted to the oxalate in ethanol.

White solid.
$C_{15}H_{17}N_3S \cdot C_2H_2O_4$.
M.p.=137°–139° C.

EXAMPLE 64

3-[(1-Methylpiperidin-4-yl)thio]-1H-indol-5-ol $R_1$=Me, $R_2$=H, $R_3$=H, $X_1$=5-OH, $X_2$=H, p=0 Formula (I)

A solution of boron tribromide (6.3 ml) in chloroform (16 ml) is added dropwise to a solution of 5-methoxy-3-[(1-methylpiperidin-4-yl)thio]-1H-indole (8 g, prepared in Example 41) in chloroform (105 ml) at 0° C. After 3 hours at room temperature, the reaction mixture is poured onto ice and rendered basic with aqueous ammonia. The organic phase is dried over sodium sulfate and concentrated. The oily residue is chromatographed on silica gel (eluent: CH$_2$Cl$_2$/EtOH/iPrNH$_2$ 79/20/1) to give 3-[(1-methylpiperidin-4-yl)thio]-1H-indol-5-ol (0.8 g), which is recrystallized from xylene.

White solid.
$C_{14}H_{18}N_2OS$.
M.p.=183°–184° C.

EXAMPLE 65

Vinyl 4-[(5-bromo-1H-indol-3-yl)thio]-piperidine-1-carboxylate $R_1$=CO$_2$—CH=CH$_2$, $R_2$=H, $R_3$=H, $X_1$=5-br, $X_2$=H, p=0   Formula (I)

Vinyl chloroformate (0.75 ml) is added dropwise to a solution of triethylamine (1.2 ml) and 5-bromo-3-(piperidin-4-ylthio)-1H-indole (2.5 g, prepared in Example 49) in dichloromethane (25 ml) at 0° C. After 2 hours at room temperature, the solution is washed with water. The organic phase is dried over magnesium sulfate and concentrated. Vinyl 4-[(5-bromo-1H-indol-3-yl)thio]-piperidine-1-carboxylate (1.8 g) is obtained after chromatography on silica gel (eluent: cyclohexane/AcOEt 70/30).

White solid.
$C_{16}H_{17}BrN_2O_2S$.
M.p.=151°–152 C.

Using an analogous method, the compounds of Examples 66 to 69 are prepared from the products of Examples 49 and 50 by reaction with acetyl chloride or ethyl, vinyl or phenyl chloroformate.

EXAMPLE 66

3-[(1-Acetylpiperidin-4-yl)thio]-5-bromo-1H-indole $R_1$=Ac, $R_2$=H, $R_3$=H, $X_1$5-Br, $X_2$H, p=0   Formula (I)

White solid.
$C_{15}H_{17}BrN_2OS$.
M.p.=155°–156° C.

EXAMPLE 67

Ethyl 4-[(5-bromo-1H-indol-3-yl)thio]piperidine-1-carboxylate $R_1$=CO$_2$Et, $R_2$=H, $R_3$=H, $X_1$=5-Br, $X_2$=H, p=0 Formula (I)

White solid.
$C_{16}H_{19}BrN_2O_2S$.
M.p.=147°–149° C. (recrystallized from acetonitrile).

EXAMPLE 68

Vinyl 4-[(5-chloro-1H-indol-3-yl)thio]piperidine-1-carboxylate $R_1$=CO$_2$—CH=CH$_2$, $R_2$=H, $R_3$=H, $X_1$=5-Cl, $X_2$=H, p=0   Formula (I)

Off-white solid.
$C_{16}H_{17}ClN_2O_2S$.
M.p.=157° C.

EXAMPLE 69

Phenyl 4-[(5-chloro-1H-indol-3-yl)thio]piperidine-1-carboxylate $R_1$=CO$_2$Ph, $R_2$=H, $R_3$=H, $X_1$=5-Cl, $X_2$=H, p=0   Formula (I)

White solid.

$C_{20}H_{19}ClN_2O_2S$.
M.p.=162°-163° C.

EXAMPLE 70

3-[(1-Methoxypiperidin-4-yl)thio]-1-methyl-1H-indole-5-carboxylic acid $R_1$=OMe, $R_2$=H, $R_3$=Me, $X_1$=5-$CO_2H$, $X_2$=H,
p=0                                              Formula (I)

A solution of butyllithium (7.1 ml, 2.5M in hexane) is added dropwise to 5-bromo-3-[(1-methoxypiperidin-4-yl)thio]-1-methyl-1H-indole (4.5 g, prepared in Example 59) in tetrahydrofuran (45 ml) at −78° C. After 1 hour at this temperature, a stream of $CO_2$ is passed into the solution. After the temperature has risen to 0° C., a solution of ammonium chloride is added. The reaction mixture is concentrated, taken up with ether and washed with water. The organic phase is dried over sodium sulfate and concentrated. The 3-[(1-methoxypiperidin-4-yl)thio]-1-methyl-1H-indole-5-carboxylic acid obtained (1.4 g) is crystallized from a small volume of isopropyl ether.
White solid.
$C_{16}H_{20}N_2O_3S$.
M.p.=170°-172° C.

EXAMPLE 71

4-[(5-Bromo-1H-indol-3-yl)thio]piperidine-1-carboxaldehyde $R_1$=CHO, $R_2$=H, $R_3$=H, $X_1$=5-Br, $X_2$=H, p=0 Formula (I)

A solution of 1,3-dicyclohexylcarbodiimide (1.7 g) in dichloromethane (4 ml) is added dropwise to a solution of 5-bromo-3-(piperidin-4-ylthio)-1H-indole (2.4 g, prepared in Example 49) and formic acid (0.3 ml) in dichloromethane (25 ml) at 0° C. The dicyclohexylurea formed is separated off and the filtrate is washed with water. The organic phase is dried over magnesium sulfate and concentrated. The 4-[(5-bromo-1H-indol-3-yl)thio]piperidine-1-carboxaldehyde obtained is recrystallized from xylene.
White solid.
$C_{14}H_{15}BrN_2OS$.
M.p.=204°-207° C.

EXAMPLE 72

Ethyl 5-bromo-3-[(1-carbethoxypiperidin-4-yl)thio]-1H-indole-1-carboxylate $R_1$=$CO_2Et$, $R_2$=H, $R_3$=$CO_2Et$, $X_1$=5-Br, $X_2$=H,
p=0                                              Formula (I)

Ethyl chloroformate (4.4 ml) is added dropwise to a toluene solution (50 ml) of 5-bromo-3-[(1-methylpiperidin-4-yl)thio]-1H-indole (5 g, prepared in Example 44) at 90° C. After refluxing for four hours, the insoluble material is filtered off and the reaction mixture is concentrated. The orange oil obtained is taken up with ether and washed with a dilute solution of hydrochloric acid. The organic phase is dried over sodium sulfate and concentrated. After chromatography on silica gel (eluent: $CH_2Cl_2$/EtOH 95/5), ethyl 5-bromo-3-[(1-carbethoxypiperidin-4-yl)thio]-1H-indole-1-carboxylate (2.5 g) is obtained in the form of an oil, which crystallizes on the addition of isopropyl ether.
White solid.
$C_{19}H_{23}BrN_2O_4S$.
M.p.=95° C.

EXAMPLE 73

3-[(1-Methoxypiperidin-4-yl)thio]-1-methyl-1H-indole-5-carboxamide $R_1$=OMe, $R_2$=H, $R_3$=Me, $X_1$=$CONH_2$, $X_2$=H,
p=0                                              Formula (I)

A solution of 3-[(1-methoxypiperidin-4-yl)thio]-1-methyl-1H-indole-5-carboxylic acid (4 g, prepared in Example 70) in a mixture of thionyl chloride (3.6 ml) and chloroform (40 ml) is refluxed for three hours. After concentration, the beige solid is dissolved in dichloromethane (30 ml) and added dropwise at 0° C. to a methanolic solution of ammonia (50 ml). After 1 hour, the reaction medium is concentrated, taken up with ethyl acetate and washed with water. The organic phase is dried over sodium sulfate and then concentrated. The residual oil is chromatographed on silica gel (eluent: AcOEt) to give 3-[(1-methoxypiperidin-4-yl)thio]-1-methyl-1H-indole-5-carboxamide (2.2 g).
White solid.
$C_{16}H_{20}N_3O_2S$.
M.p.=146° C.

EXAMPLE 74

Sodium 4-[(5-bromo-1H-indol-3-yl)thio]piperidine-1-carbodithioate $R_1$=$CS_2Na$, $R_2$=H, $R_3$=H, $X_1$=5-Br, $X_2$=H, p=0 Formula (I)

A solution of sodium hydroxide (1.4 g) and carbon disulfide (2.15 ml) in water (3 ml) is added dropwise to a solution of 5-bromo-3-(piperidin-4-ylthio)-1H-indole (10 g, prepared in Example 49) in ethanol (30 ml), kept at between 0° and 5° C. After 8 hours at room temperature, the mixture is concentrated to dryness, taken up with ethyl acetate and washed with water.
The organic phase is concentrated and taken up with ether to give sodium 4-[(5-bromo-1H-indol-3-yl)thio]piperidine-1-carbodithioate (6.1 g).
White solid.
M.p.=230° C.

EXAMPLE 75

Methyl 4-[(5-bromo-1H-indol-3-yl)thio]piperidine-1-carbodithioate $R_1$=$CS_2Me$, $R_2$=H, $R_3$=H, $X_1$=5-Br, $X_2$=H,
p=0                                              Formula (I)

A solution of sodium 4-[(5-bromo-1H-indol-3-yl)thio]piperidine-1-carbodithioate (3 g, prepared in the previous Example) and methyl iodide (0.5 ml) in 95% ethanol (15 ml) is refluxed for one hour. The orange reaction mixture is concentrated, taken up with ether and washed with water. The organic phase is dried over sodium sulfate and concentrated. After chromatography on silica gel (eluent: cyclohexane/AcOEt 70/30), methyl 4-[(5-bromo-1H-indol-3-yl)thio]piperidine-1-carbodithioate (13 g) is obtained in the form of an oil, which is taken up with pentene to give a white solid.
$C_{15}H_{17}BrN_2S_3$.
M.p.=108°-109° C.

EXAMPLE 76

3-[(1-Methoxypiperidin-4-yl)thio]-1-methyl-1H-indole-5-methanamine $R_1$=OMe, $R_2$=H, $R_3$=Me, $X_1$=5-$CH_2NH_2$,
$X_2$=H, p=0                             Formula (I)

A solution of 3-[(1-methoxypiperidin-4-yl)thio]-1-methyl-1H-indole-5-carboxamide (3.2 g, prepared in Example 73) in dry THF (40 ml) is added dropwise at 0° C. to a suspension of lithium aluminum hydride (LiAlH$_4$, 1.2 g) in anhydrous THF (200 ml). After 10 hours at room temperature, the reaction mixture is hydrolyzed at 0° C. by the addition of a saturated solution of sodium sulfate. After filtration on Celite, the solution is concentrated, taken up with ether and extracted with a dilute solution of hydrochloric acid. The aqueous phase is rendered basic with sodium hydroxide and extracted with methylene chloride. The organic phase is dried over sodium sulfate and concentrated. After chromatography on silica gel (eluent: AcOEt), 3-[(1-methoxypiperidin-4-yl)thio]-1-methyl-1H-indole-5-methanamine (1.8 g) is obtained in the form of a yellowish solid.

$C_{16}H_{23}N_3OS$.
M.p.=96° C.

EXAMPLE 77

N-[[3-[(1-Methoxypiperidin-4-yl)thio]-1-methyl-1H-indol-5-yl]methyl]methanesulfonamide $R_1$=OMe, $R_2$=H, $R_3$=Me, $X_1$=5-$CH_2NHSO_2Me$,
$X_2$=H, p=0                             Formula (I)

Mesyl chloride (0.23 ml) is added dropwise to a solution of 3-[(1-methoxypiperidin-4-yl)thio]-1-methyl-1H-indole-5-methanamine (0.8 g, prepared in the previous Example) and triethylamine (0.4 ml) in chloroform (10 ml) at 0° C. After two hours at room temperature, the solution is washed with water. The organic phase is dried over sodium sulfate and concentrated.

N-[[3-[(1-Methoxypiperidin-4-yl)thio]-1-methyl-1H-indol-5-yl]methyl]methanesulfonamide (0.4 g) is obtained after chromatography on silica gel (eluent: $CH_2Cl_2$/acetone 90/10).

White solid.
$C_{17}H_{25}N_3O_3S_2$.
M.p.=115°-116° C.

EXAMPLE 78

1-Methyl-3-[(1-methylpiperidin-4-yl)thio]-1H-indole-5-methanol $R_1$=Me, $R_2$H, $R_3$=Me, $X_1$=5-$CH_2OH$, $X_2$=H,
p=0                                       Formula (I)

A solution of 5-bromo-1-methyl-3-[(1-methylpiperidin-4-yl)thio]-1H-indole (19 g, prepared in Example 58) in THF (100 ml) is treated at −78° C. with a solution of butyllithium (31.5 ml, 2.5M in hexane). After 1 hour at this temperature, carbon dioxide is passed into the solution until it is saturated. After one hour, the reaction mixture is left to return to room temperature. The solvent is evaporated off and the residue is taken up with ether to give 1-methyl-3-[(1-methylpiperidin-4-yl)thio]-1H-indole-5-carboxylic acid (22.8 g) in the form of a yellow solid, which is used for the next step without purification.

The acid obtained (11 g) is added in portions to a suspension of lithium aluminum hydride (LiAlH$_4$, 1.6 g) in anhydrous tetrahydrofuran (60 ml) at 0° C. After 4 hours at room temperature, the reaction mixture is cooled to 0° C. and hydrolyzed with a saturated solution of sodium sulfate. The suspension is filtered on Celite and then concentrated. After purification on silica gel (eluent: $CH_2Cl_2$/ethanol 80/20), 1-methyl-3-[(1-methylpiperidin-4-yl)thio]-1H-indole-5-methanol (7.5 g) is obtained in the form of an oil.

$^1$H NMR (CDCl$_3$): 7.70 (s, 1H); 7.28 (m, 2H); 7.16 (s, 1H); 4.76 (s, 2H, $CH_2O$); 3.77 (s, 3H, NMe); 3.37 (broad s, 1H, OH); 2.85-2.75 (m, 2H, 2CHN); 2.8-2.65 (m, 1H, CHS); 2.19 (s, 3H, NMe); 2.05-1.8 (m, 4H, 2CHN+2CH); 1.75-1.5 (m, 2H, 2CH).

EXAMPLE 79

5-bromo-1-butyl-3-[(1-methylpiperidin-4-yl)thio]1H-indole $R_1$=Me, $R_2$=H, $R_3$=nBu, $X_1$=5-Br, $X_2$=H, p=0 Formula (I)

Prepared as described in Example 56 by reaction of 5-bromo-3[(1-methylpiperidin-4-yl)thio]-1H-indole (prepared in Example 44) with iodobutane.

White solid.
$C_{18}H_{25}BrN_2S$
M.p=65°-66° C.

EXAMPLE 80

Ethyl-3-[(1-methylpiperidin-4-yl)thio]-1H-indole-5-carboxylate $R_1$=Me, $R_2$=H, $R_3$=H, $X_1$=5-$CO_2Et$, $X_2$=H,
p=0.                                      Formula (I)

Prepared as described in Example 36 by reaction of 4-[(2,2-diethoxyethyl)thio]-1-methylpiperidine (prepared in Example 12) with Ethyl-4-hydrazinabenzoate hydrochloride.

White solid.
$C_{17}H_{22}N_2O_2S$
M.p.=179°-180° C.

PHARMACOLOGY

The analgesic activity of the products of the Examples was evaluated by the method involving the stretching movements caused by phenylbenzoquinone in mice, described by Siegmund et al. (1957).

Method

The intraperitoneal injection of phenylbenzo quinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the Examples are administered orally one hour before the injection of phenylbenzo quinone.

The stretching and twisting movements are counted for each mouse over an observation period of 5 minutes.

Expression of the results

The results are expressed in the form of the ID$_{50}$, i.e. the dose which makes it possible to obtain a 50% reduction in the number of pain reactions compared with the control animals.

Results

The results are presented in the Table below.

| Product of | 50% inhibitory dose (mg/kg p.o.) |
|---|---|
| Example 18 | 0.8 |
| Example 19 | 5.9 |
| Example 21 | 19.4 |
| Example 27 | 35.6 |
| Example 36 | 9.7 |
| Example 40 | 4 |
| Example 41 | 24.9 |
| Example 46 | 54.2 |
| Example 51 | 0.8 |
| Example 53 | 0.7 |
| Example 57 | 3.9 |
| Example 58 | 5.4 |
| Example 59 | 0.7 |

TOXICOLOGY

The preliminary toxicology studies performed show that the products of the Examples do not induce any deleterious effect in rats after the oral absorption of doses which can vary from 30 to 300 mg/kg.

What is claimed is:

1. A piperidinylthioindole compound of general formula (I):

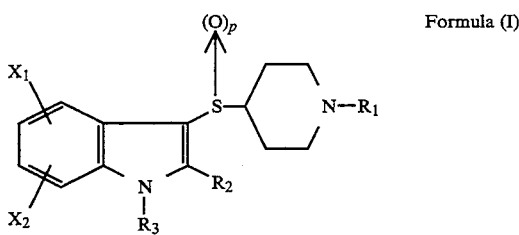

Formula (I)

in which:

$X_1$ and $X_2$ are independently:
  a hydrogen atom;
  a halogen atom;
  a lower alkyl radical having 1 to 6 carbon atoms;
  a trifluoromethyl group;
  a hydroxyl group;
  a lower O-alkyl radical having 1 to 6 carbon atoms;
  a nitrile group;
  an acid group;
  an amide group;
  a hydroxymethyl group;
  an aminomethyl group; or
  a sulfonamidomethyl group
  and can be located in the 4-, 5-, 6- or 7-position of the indole ring, $R_1$ is:
  the hydrogen atom;
  a lower alkyl radical having 1 to 6 carbon atoms;
  a methoxy group;
  a group —COR', in which R' is the hydrogen atom or a lower alkyl radical having 1 to 6 carbon atoms;
  a group —COOR";
  a group —CSSR",
  in which R" is a lower alkyl radical having 1 to 6 carbon atoms, a vinyl radical or a phenyl;
  a group —CSSM, in which M is sodium or potassium;
  a radical —$(CH_2)_n$-phenyl; or
  a radical —$(CH_2)_n$-pyrrole,
  in which n is an integer from 0 to 4, $R_2$ is:
  a hydrogen atom;
  a lower alkyl radical having 1 to 6 carbon atoms; or
  a phenyl radical which is unsubstituted or substituted by a halogen atom, $R_3$ is:
  the hydrogen atom;
  a lower alkyl radical having 1 to 6 carbon atoms;
  a group COOR", in which R" is as defined above; or
  a radical —$(CH_2)_n$-phenyl, in which the phenyl is unsubstituted or substituted by a halogen atom, n being an integer from 0 to 4, and p is an integer from 0 to 2, or a pharmaceutically acceptable addition salt.

2. A compound according to claim 1 wherein $X_2$ is the hydrogen atom and $X_1$ is a halogen atom—chlorine, bromine or fluorine—and is located in the 5-position of the indole.

3. A compound according to claim 1 wherein $R_1$ is the hydrogen atom, a methyl radical, a benzyl group, a carbonylvinyloxy group or a methoxy group.

4. A compound according to claim 1 wherein $R_2$ is the hydrogen atom or a methyl radical.

5. A compound according to claim 1 wherein $R_3$ is the hydrogen atom or a methyl radical.

6. A compound according to claim 1 wherein p is equal to zero.

7. A compound according to claim 1 which is selected from the compounds of the formulae:

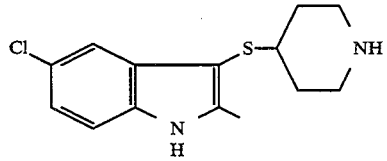

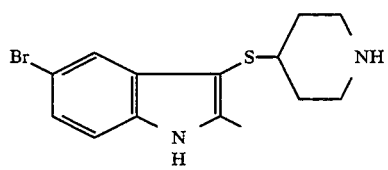

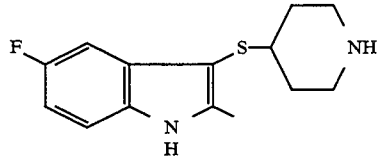

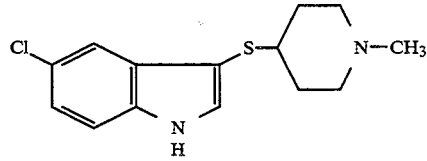

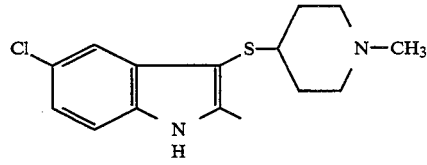

-continued

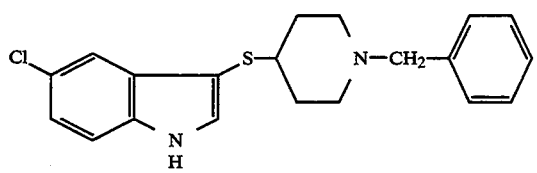

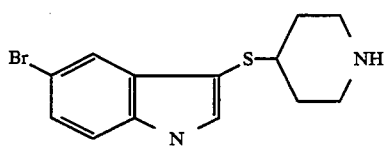

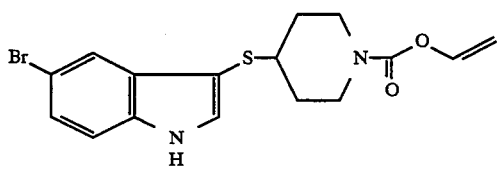

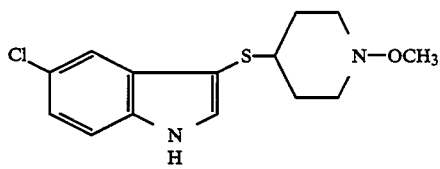

-continued

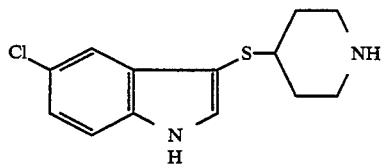

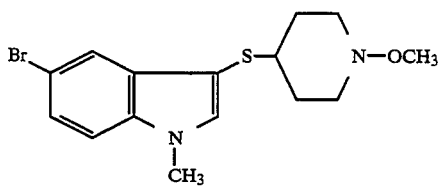

8. A pharmaceutical composition with analgesic activity, which contains a pharmaceutically effective amount of a compound of formula (I) as defined in claim 1, or a pharmaceutically acceptable addition salt incorporated in a pharmaceutically acceptable excipient, vehicle or carrier.

9. A pharmaceutical composition according to claim 8, which is formulated as a gelatin capsule or a tablet containing from 1 mg to 1000 mg of active ingredient.

10. A pharmaceutical composition according to claim 8, which is formulated as a injectable preparation containing from 0.1 to 500 mg of active ingredient.

11. A method of therapeutic treatment of mammals for pain, which comprises administering to this mammal a therapeutically effective amount of a compound of formula (I) as defined in claim 1 or a pharmaceutically acceptable addition salt thereof.

* * * * *